United States Patent [19]
Parkinson

[11] 3,979,947
[45] Sept. 14, 1976

[54] METHOD OF DETERMINING RELATIVE MOISTURE CONTENT OF EARTHY MATERIAL

[76] Inventor: Richard Parkinson, 13255 Woodcock Ave., Sylmar, Calif. 91342

[22] Filed: Apr. 14, 1975

[21] Appl. No.: 558,055

[52] U.S. Cl. .................................................. 73/73
[51] Int. Cl.² ........................................ G01N 19/10
[58] Field of Search ...................... 73/73, 88 E, 94

[56] References Cited
UNITED STATES PATENTS

| | | | |
|---|---|---|---|
| 2,907,203 | 10/1959 | Langmead | 73/73 |
| 3,353,407 | 11/1967 | Dietert et al. | 73/94 X |
| 3,533,283 | 10/1970 | Mendes da Rocha et al. | 73/94 |

OTHER PUBLICATIONS
"Moisture Density Relations of Soils Using 10-lb Rammer and 18-in Drop;" ASTM Standards; 1965, vol. 11; ASTM Designation D1557-64T.
"Tentative Methods Test for Moisture-Density Relations of Soils Using 5.5 lb Rammer and 12 in Drop," 1965, Book of ASTM Standards, vol. 11, Test No. D698-64T, Mar., 1965, pp. 300-305.
"Relationship Between California Bearing Ratio and Iowa Bearing Valve," (Appendix) LaFleur et al, Iowa State U Bull, vol. 59, No. 29; Dec. 14, 1960; pp. 289-293.

*Primary Examiner*—Herbert Goldstein
*Assistant Examiner*—John S. Appleman

[57] ABSTRACT

A method and apparatus for determining the approximate optimum moisture content required to facilitate compaction of earthy and/or granular material wherein a sample of the material to be compacted is subjected to compressive force while contained within a container and then removed therefrom and examined for behavior characteristics which give indication of its existant moisture content relative to the optimum requirement for best compaction of the sampled material.

3 Claims, 4 Drawing Figures

METHOD OF DETERMINING RELATIVE MOISTURE CONTENT OF EARTHY MATERIAL

BACKGROUND OF THE INVENTION

1. Field of the invention:

This invention relates to obtaining a quick determination of the approximate amount of moisture required to gain maximum relative compaction results from compactive effort that is being or is to be applied to earthy and/or granular material. It relates most specifically to earthwork embankments and fills and backfills where a stipulated relative compaction result is a requirement of the work. This invention also relates to the determination of this moisture requirement at the work site.

SUMMARY OF THE INVENTION

An object of the invention is to provide a test method that will indicate the need to add water to or dry out material being, or to be compacted.

Another object of the invention is to provide a test method and device that can be operated by almost anyone with a minimum amount of training.

Another object of the invention is to provide a testing device of small size and weight to render it easily portable to and useable at the work site.

Another object of the invention is to provide a test result in a very short amount of time.

Another object of the invention is to furnish a testing device that can be operated by almost anyone of normal physical strength.

In accordance with the present invention a lightweight portable device has been assembled and a test method developed rendering the device capable of achieving all the above noted objectives.

PRIOR ART

Various methods and devices have been used to determine the amount of moisture required to facilitate maximum compaction. Almost all are too complex and cumbersome to permit easy portability, therefor the samples of the material to be tested must be transported from the work site to the location of the device or devices required for the test. One of the devices and methods commonly used consists of a heavy split steel pipe and a drop bar with a cylindrical foot attached to one end of the drop bar. Companion pieces of equipment, which must be used in conjunction with the pipe and bar are (1) a weighing scale, (2) sieve screens, (3) a drying oven, (4) assorted pans, (5) mixing spoons, (6) a concrete block cast in or on the ground or some suitable firm foundation, and (7) paper and pencils to record test results and calculate the desired information. The material sample is procured from the work site then it is transported to the testing location. The sample is oven dried and then split into several weighed uniform sized portions. Water is then added in verying weighed amounts to each of the several portions. Each portion is then compacted in the pipe using the drop bar. After each portion has been compacted it is then measured for density determination. A curve is then plotted on paper showing the trend of the density versus moisture content is determined. This method is very definitive but requires a considerable lenth of time and equipment and an operator with extensive training.

In the accompanying drawing:

FIG. 3 is the tamping tool used to compress and/or compact the material being tested in the slug mold cylinder 20.

FIG. 4 is the jacking mechanism used to eject the material slug from the slug mold cylinder 20.

DESCRIPTION OF THE PREFERRED EMBODIMENT

Figure 1:
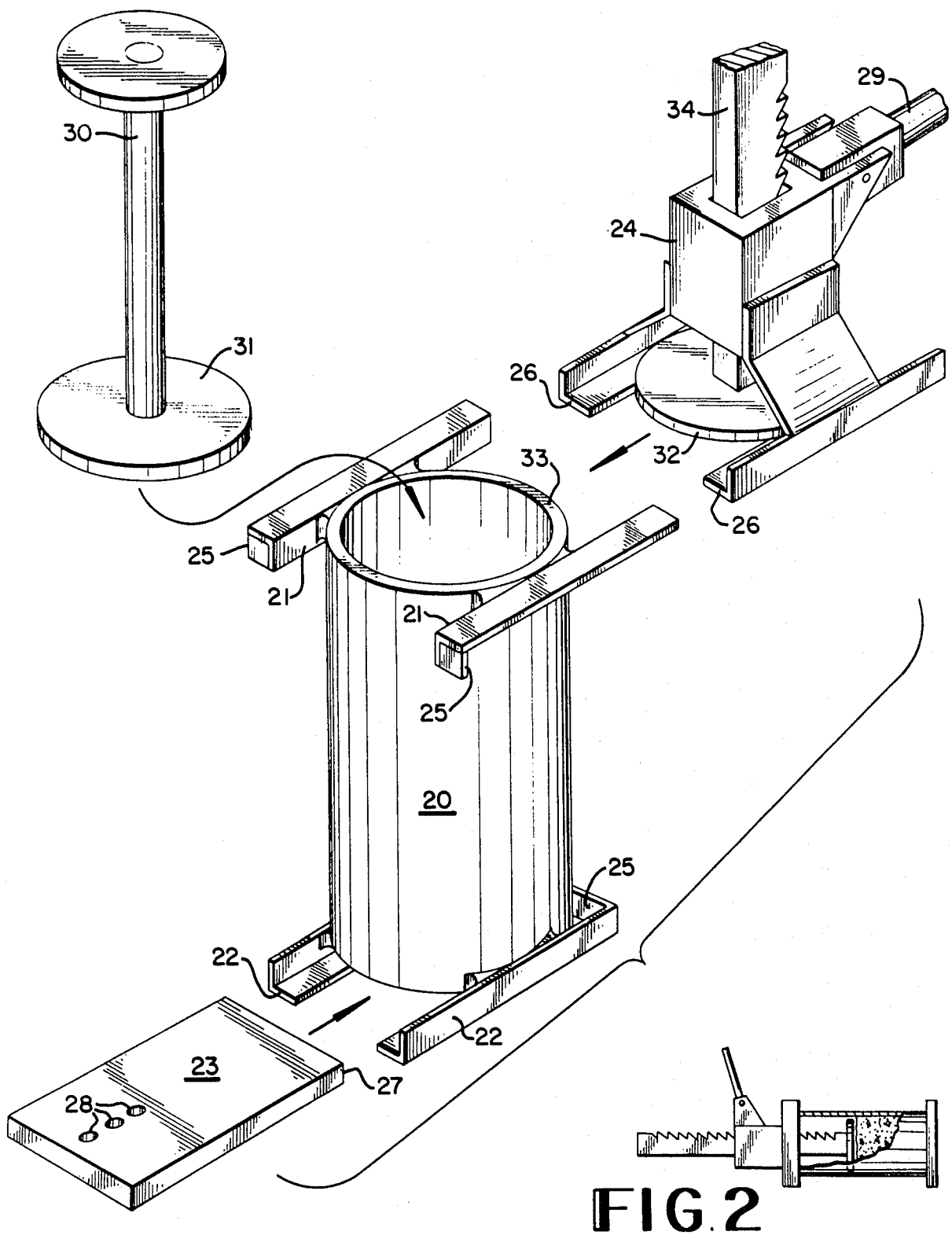
FIG. 1 is a view of the slug mold cylinder into which the material to be tested is placed.
Figure 2:
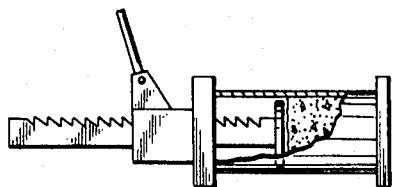
FIG. 2 is the removable closure plate for the bottom of the slug mold cylinder 20.

Refering to the accompanying drawing which forms a part of this disclosure, a slug mold cylinder 20 is shown. This cylinder 20 may be made by drilling a square or round block of metal or by cutting a section of metal pipe on or to which slots or lips 21 and 22 can be machined or welded to provide for removable attachment of the closure plates 23 and jacking mechanism 24. One end of each of the slots or lips 21 and 22 should be provided with a positive stop face 25 or surface against which the entering end of the mating flange of the jacking mechanism 26 and the entering end 27 of the closure plate 23 would not be permitted further movement and thereby positioning both the closure plate 23 and the jacking mechanism 24 for proper functioning over and/or under the barrel 33 of the slug mold cylinder 20.

The holes 28 in the closure plate 23 should be so positioned that the hooked end of the jacking mechanism's 24 handle 29 can be used as a lever against the slug mold cylinder 20 to remove the closure plate 23 after compaction of the material being tested with the tamping tool 30. The large end 31 of the tamping tool 30 and the foot 32 of the jacking mechanism 24 should be of a diameter that is slightly smaller than the inside diameter of the barrel 33 of the slug mold cylinder 20. The length of both the tamping tool 30 and the rachet bar 34 of the jacking mechanism 24 should be sufficient to extend the full depth of the slug mold cylinder's 20 barrel 33.

The apparatus is used in the following manner. The closure plate is inserted into the base of the slug mold cylinder. One-third of the sample material to be tested is inserted into the mold. The tamper is inserted into the mold cylinder, with the small end contacting the sample, and the large end is struck with 3 inch blows of a 3 pound hammer for 15 seconds as the tamper is moved over the sample surface. The tamper is reversed end — to — end and similar blows for 5 seconds are used to level the sample layer. Two repetitions form a complete three-layer sample. The plate is removed, and the mold cylinder laid horizontal. The sample is then extracted from the cylinder using the jack. The characteristics of the sample and of the plate surface are observed to determine whether the material samplied is too dry (slug breaks at layers and plate dry), optimum (slug breaks at random and plate surface damp), or too wet (slug breaks at random, is soft, and free water on plate).

What I claim is:

1. A method for determining the correct water content for compaction of earthy materials, comprising the steps of:

a. Placing a sample of the material to be tested in a vertical first tube, closed at one end by a plate, such that the sample rests on the plate;

b. inserting a second tube, with attached plates, of different sizes, at both ends, into the first tube, such that the smaller plate on the second tube contacts the sample;

c. striking the larger plate on the second tube to compact the sample;

d. reversing the position end-to-end of the second tube in the first tube;

e. striking the smaller plate on the second tube to level the surface of the sample;

f. twice repeating steps (a) through (e) so that those steps are performed a total of three times;

g. removing the plate closing the said one end of first tube:

h. placing the first tube in a substantially horizontal position;

i. extracting the conditioned composite sample from the first tube with a ratchet-operated jack;

j. evaluating the composite sample, whereby; if the sample breaks when extracted at the formed layers, is soft and porous, and the plate which closed the first tube is dry, the sample is known to be too dry; if the sample breaks when extracted at random, is hard to the touch or a light blow, and and the plate which closed the first tube is damp, the sample is known to have optimum water content; if the sample breaks when extracted at random, is soft to the touch or plastic, and water is present on the plate which closed the first tube, the sample is known to be too wet.

2. The method of claim 1, wherein step (c) comprises striking the larger plate on the second tube with three pound blows for fifteen seconds.

3. The method of claim 1, wherein step (e) comprises striking the smaller plate on the second tube with three pound blows for 5 seconds.